US012799076B2

(12) United States Patent
Chen et al.

(10) Patent No.: US 12,799,076 B2
(45) Date of Patent: Nov. 17, 2026

(54) DIPYRROLIDINE-1-ONE COMPOUNDS AND THEIR PREPARATION METHOD

(71) Applicant: WUHAN JIANMIN DAPENG PHARMACEUTICAL CO., LTD., Hubei (CN)

(72) Inventors: Fapu Chen, Wuhan (CN); Yuxin Shi, Wuhan (CN); Fakai Chen, Wuhan (CN)

(73) Assignee: Wuhan Jianmin Dapeng Pharmaceutical Co., Ltd., Hubei (CN)

( * ) Notice: Subject to any disclaimer, the term of this patent is extended or adjusted under 35 U.S.C. 154(b) by 662 days.

(21) Appl. No.: 18/208,862

(22) Filed: Jun. 12, 2023

(65) Prior Publication Data

US 2023/0322670 A1 Oct. 12, 2023

Related U.S. Application Data

(63) Continuation-in-part of application No. PCT/CN2021/073783, filed on Jan. 26, 2021.

(30) Foreign Application Priority Data

Dec. 22, 2020 (CN) ........................ 202011527195.7

(51) Int. Cl.
*C07D 207/38* (2006.01)
*A61P 35/00* (2006.01)

(52) U.S. Cl.
CPC ........... *C07D 207/38* (2013.01); *A61P 35/00* (2018.01)

(58) Field of Classification Search
CPC ............................... C07D 207/38; A61P 35/00
See application file for complete search history.

(56) References Cited

PUBLICATIONS

Kinoshita, Hideki, et al. "A New and Convenient Wittig-type Reaction for the Preparation of Pyrromethenone Derivative." Chemistry letters 22.8 (1993): 1441-1442. (Year: 1993).*

* cited by examiner

*Primary Examiner* — James H Alstrum-Acevedo
*Assistant Examiner* — Justin Christopher Sanchez
(74) *Attorney, Agent, or Firm* — JCIP GLOBAL INC.

(57) ABSTRACT

The disclosure provides a dipyrrolidine-1-one compound represented by formula 1; R is hydrogen, $C_1$-$C_5$ alkyl, or benzyl; $R_1$ is selected from thiophenyl, phenylsulfinyl, phenylsulfonyl, p-toluene sulfide, p-tosylsulfinyl, and tosyl; and $R_2$ is selected from methyl, alkoxycarbonyl, formyl, acetoxymethyl, carboxyl, and hydrogen. The compound is prepared by a compound represented by formula 2 and a compound represented by formula 3 through a condensation reaction.

5 Claims, No Drawings

DIPYRROLIDINE-1-ONE COMPOUNDS AND THEIR PREPARATION METHOD

CROSS-REFERENCE TO RELATED APPLICATIONS

This application is a continuation-in-part of International Patent Application No. PCT/CN2021/073783 with an international filing date of Jan. 26, 2021, designating the United States, now pending, and further claims foreign priority benefits to Chinese Patent Application No. 202011527195.7 filed Dec. 22, 2020. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, Cambridge, MA 02142.

BACKGROUND

The disclosure relates to the field of medicinal chemistry, and more particularly to a dipyrrolidine-1-one compound and a method for preparing the same.

Dipyrrolidene-1-one compounds are an important pharmaceutical intermediate. The known synthesis methods of dipyrrolidene-1-one compounds are complex. For example, 3-neneneba p-toluenesulfonyl ethyl-4-methyl-5-tosyl 1,5-dihydro-2H-2-pyrrolidone is condensed with pyrrolaldehyde under the catalysis of 1,8-diazabicyclo (5.4.0) undec-7-ene (DBU) and tributylphosphine to generate dipyrrolomethen-1-ones.

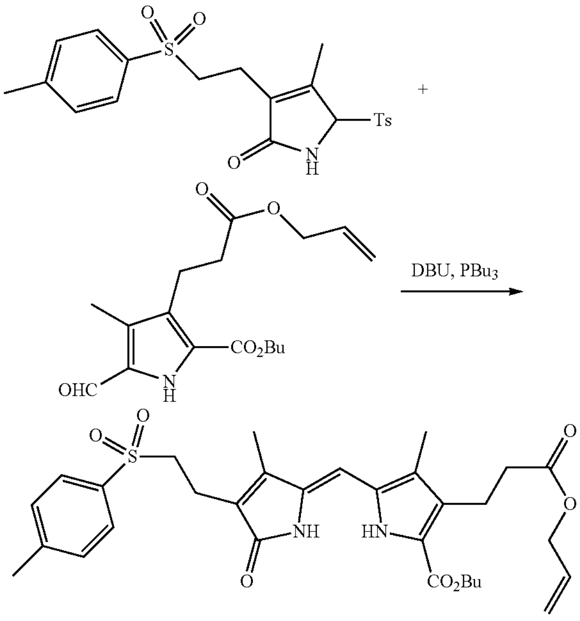

In addition, the synthesis of 5-neneneba p-toluenesulfonyl-2-pyrrolidone uses p-toluenesulfonyl vinyl as the starting material, through addition, condensation, degreasing, cyclization, bromination, hydrolysis and other steps, to obtain the product:

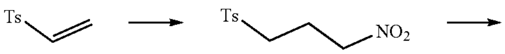

-continued

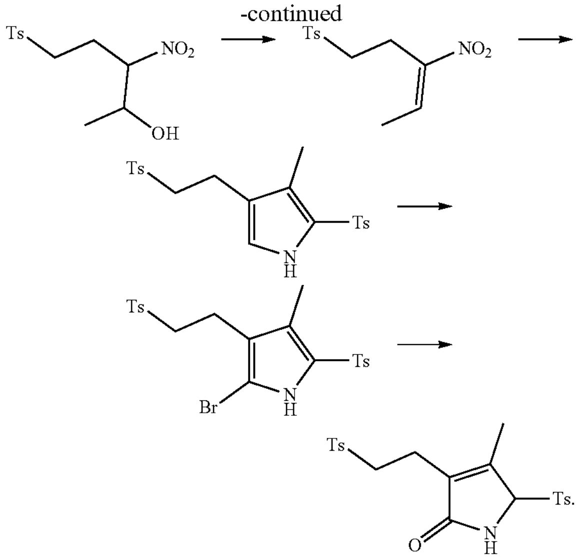

The reaction route is long, and some intermediate products have low yield and are difficult to separate (requiring column chromatography for separation), which is not suitable for industrial production. The synthesis process involves expensive reagents such as tributylphosphine and tribromotrimethylaniline, which increases the cost of raw materials. In addition, highly polluting reagents such as trifluoroacetic acid and DBU, and toxic reagents or flammable and explosive reagents such as methanesulfonyl chloride and nitromethane are also required, which limits industrial production.

SUMMARY

To solve the aforesaid problems, the disclosure provides a dipyrrolidine-1-one compound, a method for preparing the same, and use thereof In one aspect, the disclosure provides a dipyrrolidine-1-one compound represented by formula 1:

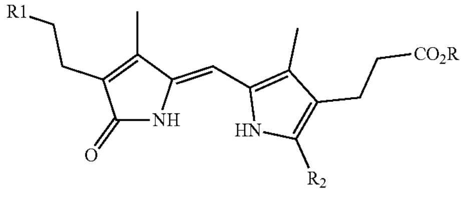

1

R is hydrogen, $C_1$-$C_5$ alkyl, or benzyl; $R_1$ is selected from thiophenyl, phenylsulfinyl, phenylsulfonyl, p-toluene sulfide, p-tosylsulfinyl, and tosyl; and $R_2$ is selected from methyl, alkoxycarbonyl, formyl, acetoxymethyl, carboxyl, and hydrogen.

In a class of this embodiment, R is hydrogen, or $C_1$-$C_5$ alkyl; $R_1$ is selected from p-toluene sulfide, p-tosylsulfinyl, and tosyl; and $R_2$ is selected from methyl, alkoxycarbonyl, and hydrogen.

In a class of this embodiment, the compound comprises one of the following formulas:

1a

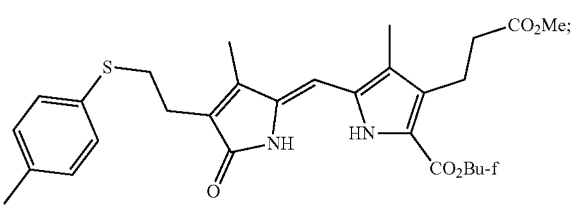

1b

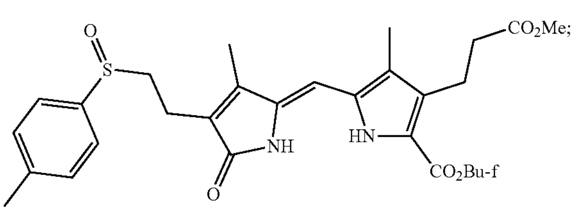

1c

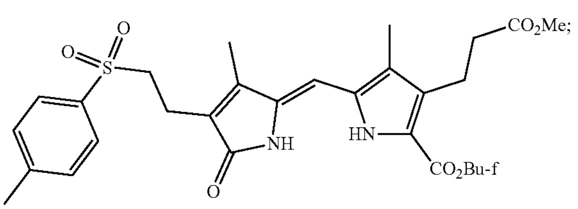

1d

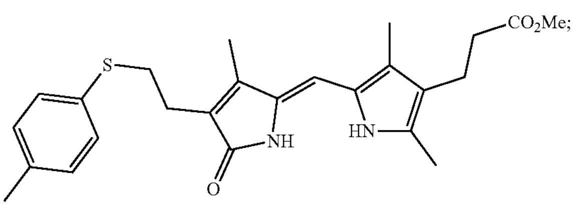

1e

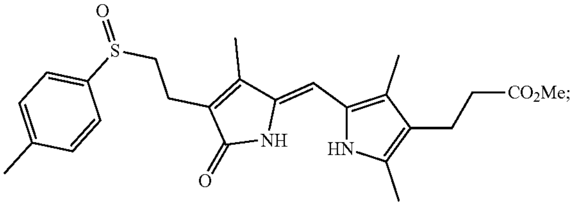

1f

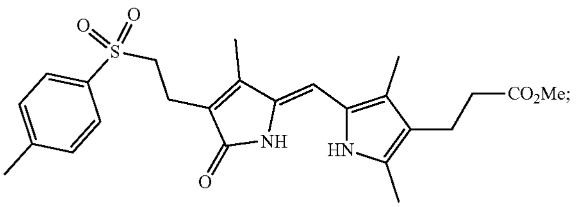

1g

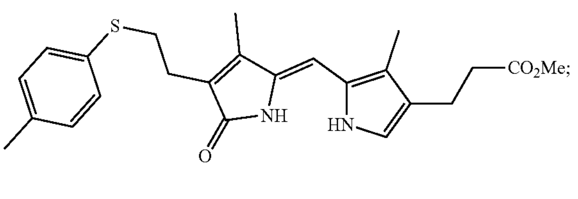

-continued

1h

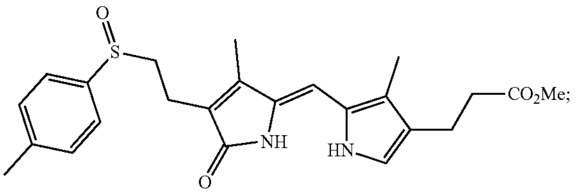

1i

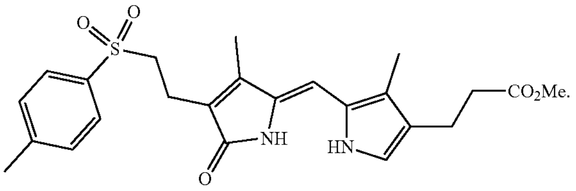

In another aspect, the disclosure provides a method for preparing the dipyrrolidine-1-one compound of claim 1, the method comprising: contacting a compound represented by formula 2 and a compound represented by formula 3 for a condensation reaction, with a reaction formula as follows:

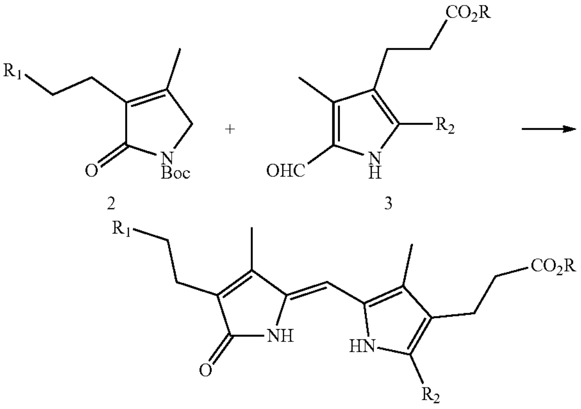

2 3

1

R is hydrogen, $C_1$-$C_5$ alkyl, or benzyl; $R_1$ is selected from thiophenyl, phenylsulfinyl, phenylsulfonyl, p-toluene sulfide, p-tosylsulfinyl, and tosyl; and $R_2$ is selected from methyl, alkoxycarbonyl, acetoxymethyl, carboxyl, and hydrogen.

In a class of this embodiment, the condensation reaction involves a solvent selected from methanol, ethanol, isopropanol, dimethylsulfoxide (DMSO), dimethyl formamide (DMF), toluene, xylene, tetrahydrofuran, methyl tetrahydrofuran, or a mixture thereof.

In a class of this embodiment, the condensation reaction involves a base as a catalyst; and the base is sodium hydroxide, potassium hydroxide, DBU, or a mixture thereof.

In a class of this embodiment, the condensation reaction is carried out at a temperature of 15-150 °C, preferably, 70-150 °C.

In a class of this embodiment, a molar ratio of the compound represented by formula 2 to the compound represented by formula 3 to the base is 1:(0.5-2):(0.2-2), preferably, 1:(0.8-1.2):(0.5-1).

The disclosure further provides a method for treating a tumor comprising administering a patient in need thereof the dipyrrolidene-1-one compound.

In a class of this embodiment, the tumor is breast cancer or lung cancer.

The following advantages are associated with the dipyrrolidine-1-one compound and the method for preparing the same of the disclosure:

1. The dipyrrolomethen-1-one compounds of the disclosure can be used to prepare drugs for treating tumors, such as breast cancer or lung cancer.
2. The disclosure provides a novel preparation method for dipyrrolidene-1-one compounds, which has simple preparation process, mild conditions, can be carried out at room temperature, with low cost. Compared with the synthesis methods of analogue compounds in existing technologies, the method of the disclosure involves no reagents such as tributylphosphine, trifluoroacetic acid, nitromethane, etc. The raw materials are simple and easy to obtain, more economical, safer, and the product is easier to separate and purify, so the method is suitable for industrial production.

DETAILED DESCRIPTION

To further illustrate the disclosure, embodiments detailing a dipyrrolidine-1 -one compound and a method for preparing the same are described below. It should be noted that the following embodiments are intended to describe and not to limit the disclosure.

Nuclear magnetic resonance (NMR) was measured using Bruker-AMX400 nuclear magnetic resonance instrument. ESI-MS was measured using Finnigan-MAT-95 mass spectrometer. All reagents are analytical pure (Sinopharm Chemical Reagent Co., Ltd.). In the following examples, 5-formyl-4-methyl-3-methoxycarbonyl-ethyl-2-pyrrolic acid tert-butyl ester (shown in formula 4) is prepared in reference to Bull Chem. Soc. Jpn., 1994, 67, 3088-3093; 3,5-dimethyl-4-methoxycarbonyl ethyl pyrrole formaldehyde (shown in formula 8) is prepared in reference to J Chem. Soc., Perkin I, 1987, 265-276; 4-methoxycarbonyl ethyl-3-methyl-2-pyrroldehyde (shown in formula 9) is prepared in reference to Tetrahedron, 1990, 42, 7599; 2,2-dimethoxypropylamine (shown in formula 13) is prepared in reference to Euro J. Med. Chem., 1995, 30, 931-942; and 4-p-toluenesulfobutyryl chloride (shown in formula 14) is prepared in reference to MedChemComm, 2017, 8, 1268-1274.

Example 1

Synthesis of 9-tert butoxycarbonyl-2,7-dimethyl-8-(2-methoxycarbonylethyl)-3-(2-p-toluenesulfoethyl)-dipyrrolidene-1-one (shown in formula 1a)

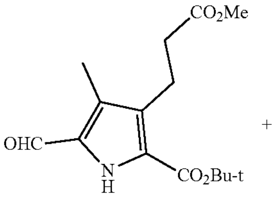

4

-continued

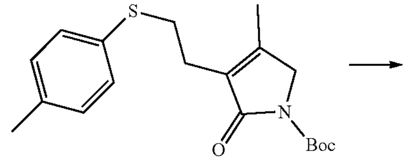

5

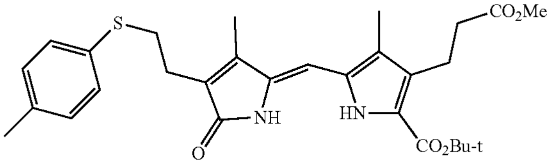

1a

Under the nitrogen atmosphere, 14.85 g (42.8 mmol) of 1-tert-butyloxycarbonyl-3-neneneba p-toluenesulfonyl ethyl-4-methyl-1,5-dihydro-2H-2-pyrrolidone (shown in Formula 5) and 11.80 g (40.0 mmol) of 5-formyl-4-methyl-3-methoxycarbonyl-ethyl 2-tert-butyl pyrrolite (shown in Formula 4) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 13.60 g of a yellow solid, with a yield of 73%. $^1$H NMR (400 MHz, $CDCl_3$): δ 1.55 (s, 9H), 2.06 (s, 3H), 2.13 (s, 3H), 2.27 (s, 3H), 2.53 (t, J=8.0 Hz, 2H), 2.80 (t, J=7.2 Hz, 2H), 3.03 (t, J=8.0 Hz, 2H), 3.15 (t, J=7.2 Hz, 2H), 3.71 (s, 3H), 6.02 (s, 1H), 7.03 (d, J=8.1 Hz, 2H), 7.23 (d, J=8.1 Hz, 2H), 9.91 (s, 1H), 10.17 (s, 1H); ESI-Mass: 546.63 $(M+Na)^+$.

Example 2

Synthesis of 9-tert-butyloxycarbonyl-3,7-dimethyl-8-(2-methoxycarbonyl ethyl)-2-(2-p-tolylene sulfonyl group ethyl)-dipyrrolomethen-1-one (shown in formula 1b)

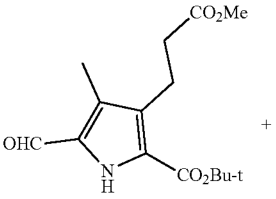

4

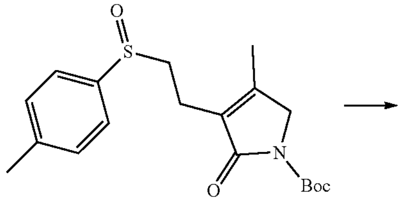

6

-continued

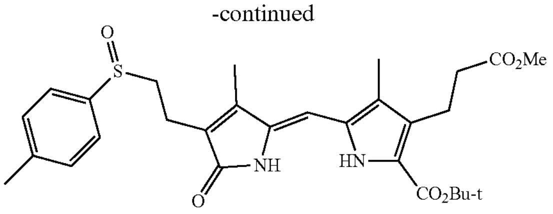

1b

Under the nitrogen atmosphere, 3.47 g (10 mmol) of 1-tert-butoxycarbonyl-3-p-tolylene sulfonyl group ethyl-4-methyl-1,5-dihydro-2H-2-pyrrolidone (shown in Formula 6) and 3.00 g (10.2 mmol) of 5-formyl-4-methyl-3-methoxy-carbonyl-ethyl 2-tert-butyl pyrrolite (shown in Formula 4) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 3.56 g of a yellow solid, with a yield of 66%. $^1$H NMR (400 MHz, $CDCl_3$): δ 1.57 (s, 9H), 2.08 (s, 3H), 2.15 (s, 3H), 2.30 (s, 3H), 2.54 (t, J=8.0 Hz, 2H), 2.80 (t, J=7.2 Hz, 2H), 3.03 (t, J=8.0 Hz, 2H), 3.17 (t, J=7.2 Hz, 2H), 3.70 (s, 3H), 6.00 (s, 1H), 7.03 (d, J=8.0 Hz, 2H), 7.23 (d, J=8.0 Hz, 2H), 9.89 (s, 1H), 10.20 (s, 1H); ESI-Mass: 563.45 $(M+Na)^+$.

Example 3

Synthesis of 9-tert-butyloxycarbonyl-3,7-dimethyl-8-(2-methoxycarbonyl ethyl)-2-(2-neneneba p-toluenesulfonyl ethyl)-dipyrrolomethen-1-one (shown in formula 1c)

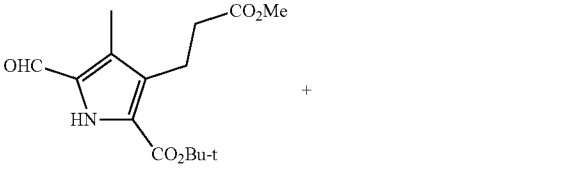

4

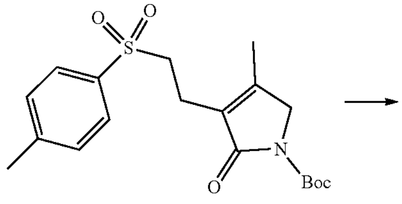

7

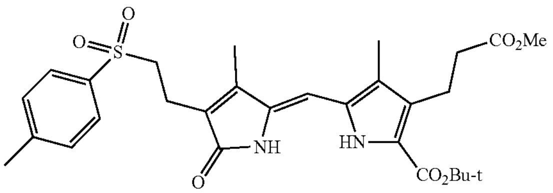

1c

Under the nitrogen atmosphere, 2.8 g (10 mmol) of 1-tert-butyloxycarbonyl-3-neneneba p-toluenesulfonyl ethyl-4-methyl-1,5-dihydro-2H-2-pyrrolidone (shown in Formula 7) and 3.00 g (10.2 mmol) of 5-formyl-4-methyl-3-methoxycarbonyl-ethyl 2-tert-butyl pyrrolite (shown in Formula 4) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 3.31 g of a yellow solid, with a yield of 56%. $^1$H NMR (400 MHz, $CDCl_3$): δ 1.56 (s, 9H), 2.11 (s, 3H), 2.14 (s, 3H), 2.35 (s, 3H), 2.52 (t, J=8.10 Hz, 2H), 2.87 (t, J=7.18 Hz, 2H), 2.99 (t, J=8.07 Hz, 2H), 3.45 (t, J =7.30 Hz, 2H), 3.67 (s, 3H), 5.96 (s, 1H), 6.66 (s, 1H), 7.26 (d, J=8.23 Hz, 2H), 7.72 (d, J=8.23 Hz, 2H), 9.16 (s, 1H), 9.49 (s, 1H); ESI-Mass: 579.27 $(M+Na)^+$.

Example 4

Synthesis of 3,7,9-trimethyl-8-(2-methoxycarbonylethyl)-2-(2-p-toluenesulfoethyl)-dipyrrolidene-1-one (shown in formula 1d)

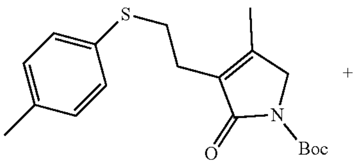

5

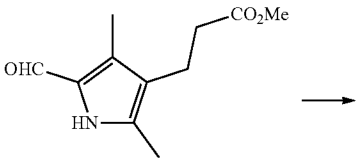

8

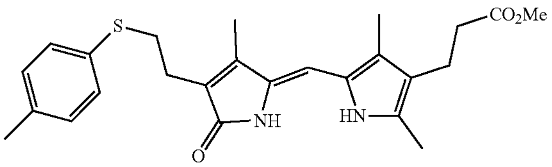

1d

Under the nitrogen atmosphere, 3.47 g (10 mmol) of 1-tert-butyloxycarbonyl-3-neneneba p-toluenesulfonyl ethyl-4-methyl-1,5-dihydro-2H-2-pyrrolidone (shown in Formula 5) and 2.30 g (11.0 mmol) of 3,5-dimethyl-4-methoxycarbonyl ethyl pyrrolaldehyde (shown in Formula 8) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 2.32 g of a yellow solid, with a yield of 53%. $^1$H NMR (400 MHz, $CDCl_3$): δ 2.09 (s, 3H), 2.13 (s, 3H), 2.28 (s, 3H), 2.35 (s, 3H), 2.44 (t, J=7.6 Hz, 2H), 2.69-2.64 (m, 4H), 3.08 (t, J=7.6 Hz, 2H), 3.67 (s, 3H), 6.14 (s, 1H), 7.06 (d, J=8.0 Hz, 2H), 7.23 (d, J=8.0 Hz, 2H), 9.45 (s, 1H), 10.17 (s, 1H); ESI-Mass: 461.50 $(M+Na)^+$.

Example 5

Synthesis of 3,7,9-trimethyl-8-(2-methoxycarbonyl ethyl)-2-(2-p-tolylene sulfonyl group ethyl)-dipyrrolidone (shown in formula 1e)

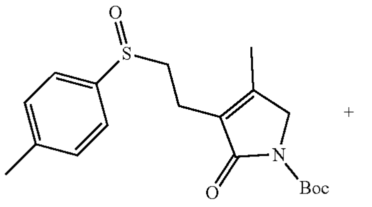

6

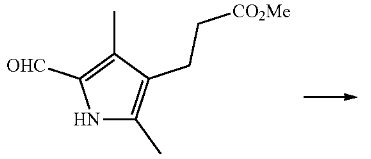

8

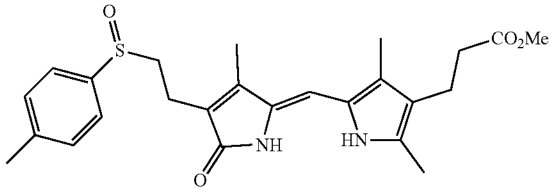

1e

Under the nitrogen atmosphere, 3.63 g (10.0 mmol) of 1-tert-butyloxycarbonyl-3-p-tolylene sulfonyl group ethyl-4-methyl-1,5-dihydro-2H-2-pyrrolidone (shown in Formula 6) and 2.30 g of 3,5-dimethyl-4-methoxycarbonyl-ethyl-2-pyrrolialdehyde (shown in Formula 8) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 2.58 g of a yellow solid, with a yield of 57%. $^1$H NMR (400 MHz, $CDCl_3$): δ 2.10 (s, 3H), 2.13 (s, 3H), 2.28 (s, 3H), 2.36 (s, 3H), 2.45 (t, J=7.4 Hz, 2H), 2.68-2.65 (m, 4H), 3.09 (t, J=7.6 Hz, 2H), 3.67 (s, 3H), 6.14 (s, 1H), 7.07 (d, J=8.0 Hz, 2H), 7.22 (d, J=8.0 Hz, 2H), 9.44 (s, 1H), 10.16 (s, 1H); ESI-Mass: 477.22 $(M+Na)^+$.

Example 6

Synthesis of 3,7,9-trimethyl-8-(2-carboxyethyl) -2-(2-p-toluenesulfoethyl)-Dipyrrolidene-1-one (shown in formula 1f)

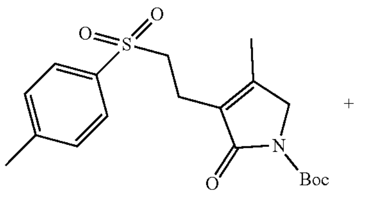

6

-continued

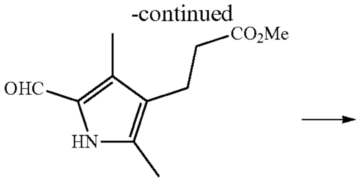

8

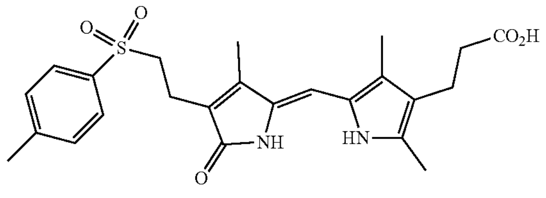

1f

Under the nitrogen atmosphere, 3.47 g (10.0 mmol) of 1-tert-butoxycarbonyl-3-p-toluenesulfonyl-ethyl-4-methyl-1,5-dihydro-2H-2-pyrrolidone (shown in Formula 7) and 2.30 g (11.0 mmol) of 3,5-dimethyl-4-methoxycarbonyl-ethyl-2-pyrrolialdehyde (shown in Formula 8) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 2.22 g of a yellow solid, with a yield of 65%. $^1$H NMR (400 MHz, DMSO-$D_6$): δ 2.11 (s, 3H), 2.15 (s, 3H), 2.25 (s, 3H), 2.35 (s, 3H), 2.42 (t, J=7.6 Hz, 2H), 2.62-2.66 (m, 4H), 3.10 (t, J=7.6 Hz, 2H), 6.15 (s, 1H), 7.08 (d, J=8.0 Hz, 2H), 7.21 (d, J=8.0 Hz, 2H), 9.40 (s, 1H), 10.11 (s, 1H); ESI-Mass: 423.32 $(M-1)^+$.

Example 7

Synthesis of 3,7-dimethyl-8-(2-ethoxycarbonylethyl) -2-(2-p-toluenesulfoethyl)-dipyrrolidene-1-one (shown in formula 1 g)

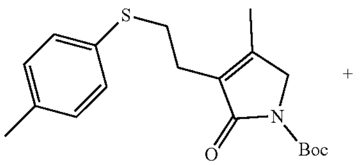

5

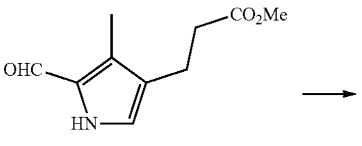

9

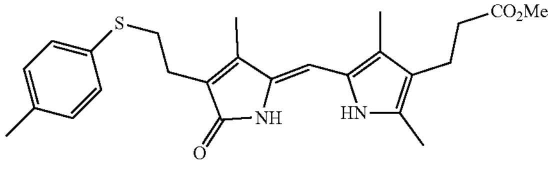

1g

Under the nitrogen atmosphere, 3.47 g (10.0 mmol) of 1-tert-butyloxycarbonyl-3-neneneba p-toluenesulfonyl ethyl-4-methyl-1,5-dihydro-2H-2-pyrrolidone (shown in Formula 5) and 2.14 g (11.0 mmol) of 4-methoxycarbonylethyl-3-methyl-2-pyrrolaldehyde (shown in Formula 9) were mixed and dissolved in 20 mL of toluene, and then 4.0 mL of DBU was added. The resulting mixture was stirred at 90 °C for 5 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 2.8 g of a yellow solid, with a yield of 66%. $^1$H NMR (400 MHz, $CDCl_3$): δ 1.26 (t, J=7.4 Hz, 3H), 2.12 (s, 3H), 2.16 (s, 3H), 2.27 (s, 3H), 2.52 (t, J=8.3 Hz, 2H), 2.71-2.76 (m, 4H), 3.14 (t, J=7.2 Hz, 2H), 4.15 (q, J=7.4 Hz, 2H), 6.23 (s, 1H), 6.79 (d, J=2.4 Hz, 2H), 7.05 (d, J=8.0 Hz, 2H), 7.25 (d, J=8.0 Hz, 2H), 10.51 (s, 1H), 11.15 (s, 1H); ESI-Mass: 461.20 (M+Na)+.

Example 8

Synthesis of 3,7,9-trimethyl-8-(2-methoxycarbonyl ethyl)-2-(2-p-tolylene sulfonyl group ethyl)-dipyrrolidone (shown in formula 1h)

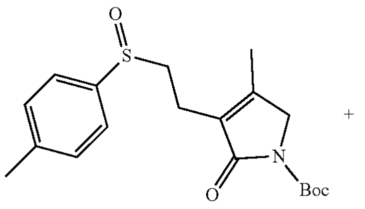

6

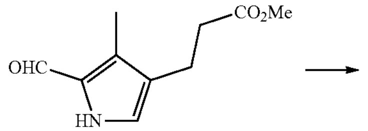

9

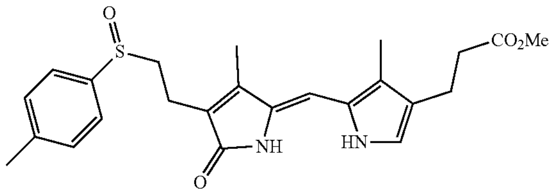

1h

Under the nitrogen atmosphere, 3.63 g of 1-tert-butoxycarbonyl-3-p-tolylene sulfonyl group ethyl-4-methyl-1,5-dihydro-2H-2-pyrrolidone (shown in Formula 6) and 1.95 g of 4-methoxycarbonylethyl-3-methyl-2-pyrrolaldehyde (shown in Formula 9) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 2.24 g of a yellow solid, with a yield of 51%. $^1$H NMR (400 MHz, $CDCl_3$): δ $^1$H NMR (400 MHz, $CDCl_3$): δ1.26 (t, J=7.2 Hz, 3H), 2.11 (s, 3H), 2.16 (s, 3H), 2.28 (s, 3H), 2.57 (t, J=8.0 Hz, 2H), 2.70-2.77 (m, 4H), 3.14 (t, J=7.2 Hz, 2H), 4.16 (q, J =7.2 Hz, 2H), 6.22 (s, 1H), 6.79 (d, J=2.4 Hz, 2H), 7.07 (d, J=8.0 Hz, 2H), 7.25 (d, J=8.0 Hz, 2H), 10.51 (s, 1H), 11.15 (s, 1H); ESI-Mass: 477.22 $(M+Na)^+$.

Example 9

Synthesis of 3,7,9-trimethyl-8-(2-methoxycarbonyl ethyl)-2-(2-neneneba p-toluenesulfonyl ethyl)-dipyrrolomethen-1-one (shown in formula 1i)

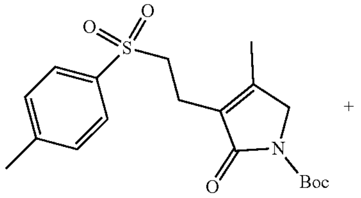

7

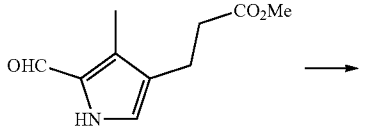

9

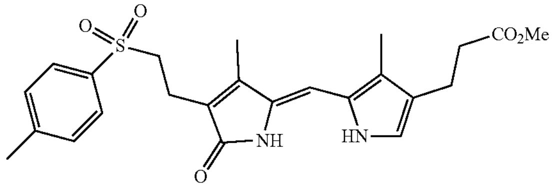

1i

Under the nitrogen atmosphere, 3.63 of 1-tert-butoxycarbonyl-3-p-tolylene sulfonyl group ethyl-4-methyl-1,5-dihydro-2H-2-pyrrolidone (shown in Formula 7) and 1.95 g of 4-methoxycarbonylethyl-3-methyl-2-pyrrolaldehyde (shown in Formula 9) were mixed and dissolved in 20 mL of toluene, and then 4.0 mL of DBU was added. The resulting mixture was stirred at 90 °C for 10 hours, cooled, and evaporated to remove solvent under reduced pressure. The residue was dissolved with dichloromethane, and acidified with dilute hydrochloric acid to pH 5. The dichloromethane layer was collected, concentrated, and recrystallized with ethanol to obtain 2.24 g of a yellow solid, with a yield of 51%. $^1$H NMR (400 MHz, $CDCl_3$): δ $^1$H NMR (400 MHz, $CDCl_3$): δ1.26 (t, J=7.2 Hz, 3H), 2.11 (s, 3H), 2.16 (s, 3H), 2.28 (s, 3H), 2.57 (t, J=8.0 Hz, 2H), 2.70-2.77 (m, 4H), 3.14 (t, J=7.2 Hz, 2H), 4.16 (q, J =7.2 Hz, 2H), 6.22 (s, 1H), 6.79 (d, J=2.4 Hz, 2H), 7.07 (d, J=8.0 Hz, 2H), 7.25 (d, J=8.0 Hz, 2H), 10.51 (s, 1H), 11.15 (s, 1H); ESI-Mass: 477.22 $(M+Na)^+$.

Example 10

1. Synthesis of 1-tert butoxycarbonyl-3-(2-p-toluenesulfonyl ethyl) -4-methyl-1H-2 (5H) pyrrolidone (shown in formula 7)

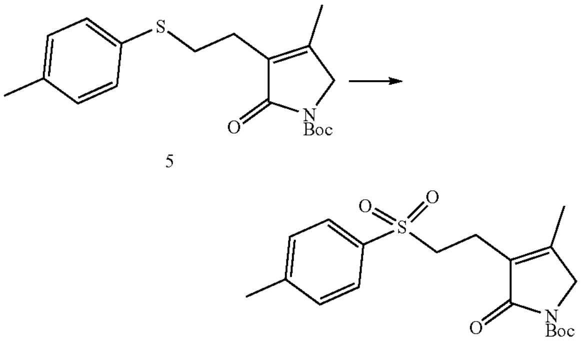

5

7

3.47 g of the shown in formula 5 was dissolved in 50 mL of methanol, and then 5.7 mL of 30% hydrogen peroxide was added. The resulting mixture was kept at 75 °C for 2 hours, washed with a 10% sodium bisulfite solution, extracted with dichloromethane. The organic layer was collected, washed with saturated salt water, dried with anhydrous sodium sulfate, filtered, and concentrated to obtain 3.47 g of light yellow oily substance, with a yield of 91%. The product was directly used for next reaction.

2. Synthesis of N-tert butoxycarbonyl-3-(2-p-toluenesulfonyl ethyl) -4-methyl-1H-2 (5H) pyrrolidone (shown in formula 6)

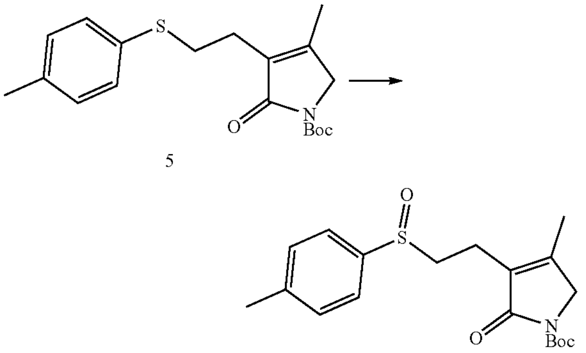

5

6

3.47 g of the compound shown in formula 5 was dissolved in 50 mL of dichloromethane, and cooled to 0 °C. 2.21 g of 85% m-chloro perbenzoic acid was added in batches to the resulting mixture, and the temperature was controlled below 5 °C. Under the temperature, the mixture was stirred for 2 hours, and washed with 10% sodium bisulfite solution. The organic layer was collected, washed with saturated salt water, dried with anhydrous sodium sulfate, filtered, and concentrated to obtain 3.48 g of a light yellow oily product, with a yield of 95%, which was directly used for next reaction.

3. Synthesis of N-tert butoxycarbonyl-3-(2-p-toluenesulfoethyl) -4-methyl-1H-2 (5H) pyrrolidone (shown in formula 5)

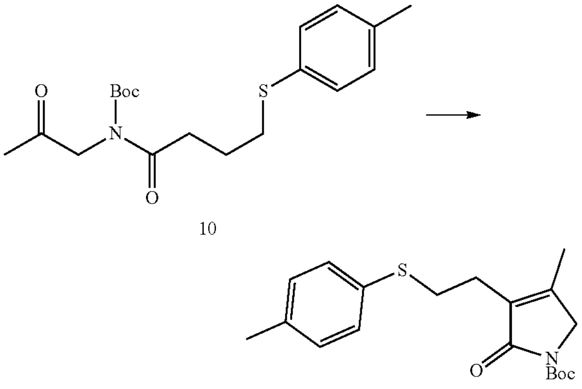

10

5

6.80 g of the compound shown in formula 10 was dissolved in 50 mL of a dimethylsulfoxide (DMSO) solution comprising 3.0 g of sodium hydroxide, stirred at room temperature for 30 minutes. The resulting mixture was poured into 100 mL of ice water, extracted with ethyl acetate, washed with dilute hydrochloric acid to neutral, washed with saturated salt water, dried with anhydrous sodium sulfate, filtered, concentrated, and recrystallized with ethanol to obtain 6.0 g of an earthy yellow solid with a yield of 84%. $^1$H NMR (400 MHz, $CDCl_3$): δ1.55 (s, 9H), δ1.95 (s, 3H), 2.30 (s, 3H), 2.57 (t, J=7.2 Hz, 2H), 3.11 (t, J=7.2 Hz, 2H), 4.03 (s, 2H), 7.08 (d, J=8.0 Hz, 2H), 7.25 (d, J=8.0 Hz, 2H); ESI-Mass: 717.14 $(2M+Na)^+$.

4. Synthesis of N-acetonyl-N-tert-butyloxycarbonyl-4-p-toluenesulfobutylamide (shown in formula 10)

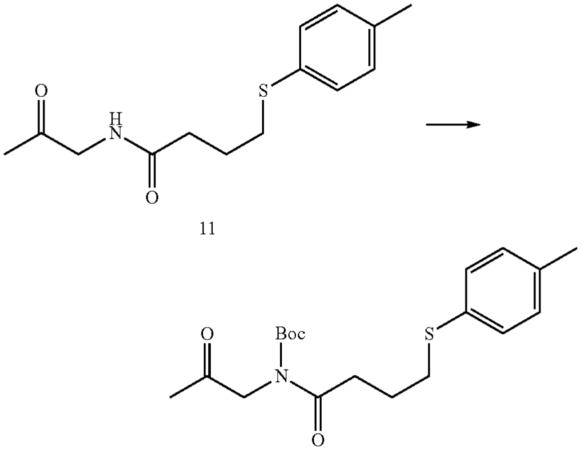

11

10

8 g of the compound shown in formula 11 was dissolved in 50 mL of dichloromethane, and then 8.0 g of DMAP was added. The temperature of the resulting mixture was lowered to 0 °C. 13.2 g of Boc2O dissolved in 90 mL of dichloromethane was slowly added to the mixture, and the temperature was controlled not to exceed 5 °C. The mixture was stirred for 10 hours at 15-30 °C, and then poured into 100 mL of ice water. The aqueous phase was acidified to pH3 with dilute hydrochloric acid, and the organic layer was separated, washed with saturated sodium bicarbonate and salt water successively, dried over anhydrous sodium sulfate, filtered and concentrated to obtain 10.81 g of a light yellow liquid, which was n-acetone-n-tert-butylcarbonyl-4-p-toluene thiobutyl amide, with a yield of 99%. $^1$H NMR (400 MHz, $CDCl_3$): δ1.47 (s, 9H), 1.93-1.97 (m, 2H), 2.14 (s, 3H), 2.30 (s, 3H), 2.93 (t, J=6.0 Hz, 2H),3.08 (t, J=7.2 Hz, 2H), 4.49 (s, 2H), 7.08 (d, J=8.2 Hz, 2H), 7.25 (d, J=8.2 Hz, 2H); ESI-Mass: 387.97 $(M+Na)^+$.

5. Synthesis of N-acetone -4-p-toluene thiobutyl amide (shown in formula 11)

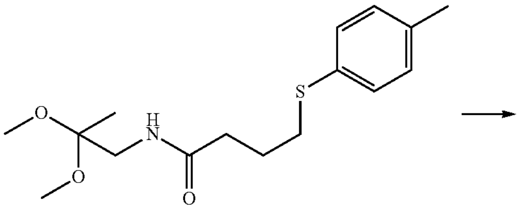

12

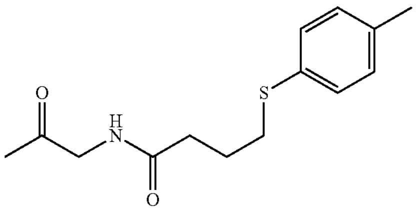

11

11.73 g of the compound shown in Formula 12 was dissolved in 50 mL of dichloromethane, and 8.0 g (10.8 mmol) of 5% dilute hydrochloric acid was added. The mixture was stirred at room temperature for 4 hours, and rested. The dichloromethane layer was collected, washed with saturated salt water and water in turn, dried with anhydrous sodium sulfate, filtered, and concentrated, to yield 10.20 g white solid, that is, N-acetone-4-p-toluene-thiobutyl amide, with a yield of 96%. $^1$H NMR (400 MHz, $CDCl_3$): δ1.92-1.97 (m, 2H), 2.20 (s, 3H), 2.31 (s, 3H), 2.39 (t, 6.8 Hz, 2H), 2.93 (t, J=6.8 Hz, 2H), 4.14 (d, J=4.0 Hz, 2H), 6.22 (s, 1H), 7.09 (d, J=4.0 Hz, 2H), 7.26 (d, J=8.0 Hz, 2H); ESI-Mass: 266.0 $(M+H)^+$.

6. Synthesis of N-(2, 2-dimethoxy-propyl)-4-p-toluene thiobutyl amide (shown in formula 12)

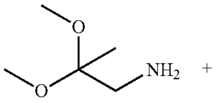

13

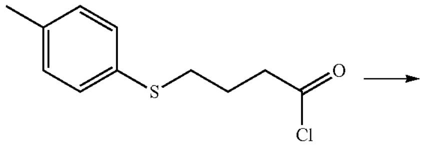

14

-continued

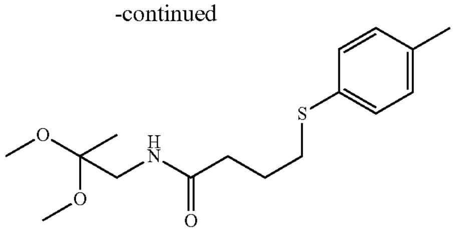

12

6.80 g of 2, 2-dimethoxy-propylamine (57.1 mmol, as shown in formula 13) was dissolved in 20 mL of methylene chloride, and then 6.10 g of triethylamine (60.4 mmol) was added and cooled to 0 °C. 13.03 g (57.1 mmol) of 4-p-toluene thiobutyl chloride (shown in Formula 14) dissolved in 20 mL of dichloromethane was added to the resulting mixture, and the temperature was controlled below 5 °C. The mixture was stirred at 20-30 °C for 10 hours, and filtered to obtain N-(2, 2-dimethoxy-propyl) -4-p-toluene thiobutyl amide. The filter cake was washed with methylene chloride and the filtrate was directly used for next reaction.

Example 11

1. Experimental Method:

Antitumor activity test: Sulfonyl rhodamine B (SRB) method was used to determine the in vitro anti-tumor activity of A-549 breast cancer cells. A-549 human breast cancer cells in logarithmic growth were inoculated into a 96 well microculture plate with the amount of 90 μL/well. 24 hours later, the solutions respectively containing the compounds 1a, 1b, 1c, 1d, 1e, 1f, 1g, 1h, and 1i of the disclosure were added to the wells with each 10 μL/well, and three wells for each concentration. A cell-free zero adjustment hole was also provided. The concentrations of the compounds 1a, 1b, 1c, 1d, 1e, 1f, 1g, 1h, and 1i in corresponding solution were all $10^{-5}$ M. The tumor cells were cultured at 37 °C under 5% $CO_2$ for 72 hours. The culture medium was discarded, and 100 μL/well of 10% TCA was added to the cells for fixing at 4 °C for 1 hour. The cells were washed three times with distilled water, and dried naturally. 4 mg/mL SRB (Sigma) staining solution of 100 μL/well was added for staining at room temperature for 15 minutes, washed three times with 1% acetic acid aqueous solution, and dried naturally. 100 μL/well of 10 mM Tris base aqueous solution was further added. Then, the optical density (OD560) value was measured using an enzyme-linked immunosorbent assay at a wavelength of 560 nm. The inhibition rate of the tested compounds on tumor cell growth was calculated according to the formula: (control group OD value-administration group OD value)/control group OD value×100%.

2. The Experimental Results are Shown in Table 1.

TABLE 1

Results of the inhibitory rates of compounds 1a, 1b, 1c, 1d, 1e, 1f, 1g, 1h, and 1i solutions with concentrations of $10^{-5}$ M on tumor cell growth

| Compound | Inhibitory rates on tumor cell growth (%) | Compound | Inhibitory rates on tumor cell growth (%) |
|---|---|---|---|
| 1a | 72.3 | 1b | 57.0 |
| 1c | 34.4 | 1d | 37.8 |

TABLE 1-continued

Results of the inhibitory rates of compounds 1a, 1b, 1c, 1d, 1e, 1f, 1g, 1h, and 1i solutions with concentrations of $10^{-5}$ M on tumor cell growth

| Compound | Inhibitory rates on tumor cell growth (%) | Compound | Inhibitory rates on tumor cell growth (%) |
| --- | --- | --- | --- |
| 1e | 63.4 | 1f | 23.5 |
| 1g | 35.6 | 1h | 11.7 |
| 1i | 28.4 | | |

3. Conclusion

Under the above concentrations, the compound has certain inhibitory activity on A-549 human breast cancer cells. Therefore, the dipyrrolomethen-1 -one of the disclosure can be used to prepare drugs or lead compound for treating tumors, especially drugs and lead compound for treating breast cancer and lung cancer.

It will be obvious to those skilled in the art that changes and modifications may be made, and therefore, the aim in the appended claims is to cover all such changes and modifications.

What is claimed is:

1. A method for preparing a dipyrrolidine-1-one compound, the method comprising: contacting a compound represented by formula 2 and a compound represented by formula 3 for a condensation reaction, with a reaction formula as follows:

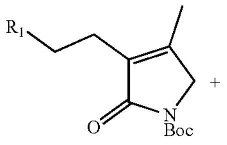

2

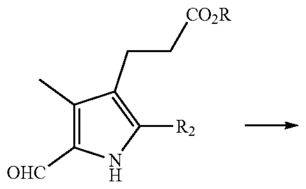

3

-continued

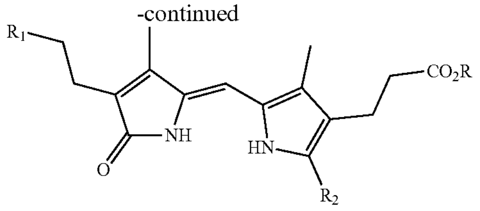

1 wherein:

R is hydrogen, $C_1$-$C_5$ alkyl, or benzyl;

$R_1$ is selected from thiophenyl, phenylsulfinyl, phenylsulfonyl, p-toluene sulfide, p-tosylsulfinyl, and tosyl; and $R_2$ is selected from methyl, alkoxycarbonyl, acetoxymethyl, carboxyl, and hydrogen, wherein the dipyrrolidine-1-one compound is represented by formula 1:

1

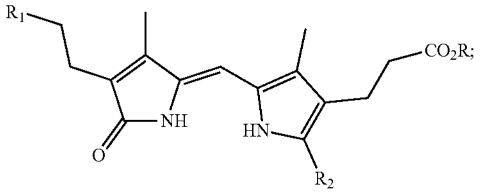

wherein:

R is hydrogen, $C_1$-$C_5$ alkyl, or benzyl;

$R_1$ is selected from thiophenyl, phenylsulfinyl, phenylsulfonyl, p-toluene sulfide, p-tosylsulfinyl, and tosyl; and $R_2$ is selected from methyl, alkoxycarbonyl, formyl, acetoxymethyl, carboxyl, and hydrogen.

2. The method of claim 1, wherein the condensation reaction involves a solvent selected from methanol, ethanol, isopropanol, dimethylsulfoxide (DMSO), dimethyl formamide (DMF), toluene, xylene, tetrahydrofuran, methyl tetrahydrofuran, or a mixture thereof.

3. The method of claim 1, wherein the condensation reaction involves a base as a catalyst; and the base is sodium hydroxide, potassium hydroxide, 1,8-diazabicyclo (5.4.0) undec-7-ene (DBU), or a mixture thereof.

4. The method of claim 1, wherein the condensation reaction is carried out at a temperature of 15-150 °C.

5. The method of claim 3, wherein a molar ratio of the compound represented by formula 2 to the compound represented by formula 3 to the base is 1:(0.5-2):(0.2-2).

* * * * *